(12) United States Patent
Kroll

(10) Patent No.: US 6,169,923 B1
(45) Date of Patent: Jan. 2, 2001

(54) IMPLANTABLE CARDIOVERTER-DEFIBRILLATOR WITH AUTOMATIC ARRHYTHMIA DETECTION CRITERIA ADJUSTMENT

(75) Inventor: Mark W. Kroll, Orono, MN (US)

(73) Assignee: Pacesetter, Inc., Sylmar, CA (US)

(*) Notice: Under 35 U.S.C. 154(b), the term of this patent shall be extended for 0 days.

(21) Appl. No.: 09/298,709

(22) Filed: Apr. 23, 1999

(51) Int. Cl.[7] ........................ A61N 1/39
(52) U.S. Cl. ........................ 607/5; 600/515
(58) Field of Search .......... 607/5, 14; 600/515, 600/518

(56) References Cited

U.S. PATENT DOCUMENTS

| | | | |
|---|---|---|---|
| 5,179,945 | 1/1993 | Van Hofwegen et al. | 128/419 D |
| 5,188,105 | 2/1993 | Keimel | 128/419 D |
| 5,191,884 | 3/1993 | Gilli et al. | 128/419 D |
| 5,403,354 | * 4/1995 | Adams et al. | 607/5 |
| 5,458,619 | 10/1995 | Olson | 607/4 |

\* cited by examiner

*Primary Examiner*—George R. Evanisko

(57) ABSTRACT

An arrhythmia detection system provides automatic detection criteria adjustment in an implantable cardioverter-defibrillator that applies arrhythmia terminating electrical energy to a heart responsive to detection of the arrhythmic episode of the heart. A first detector detects arrhythmic episodes of the heart in accordance with detection criteria. A second detection confirms the detection of each arrhythmic episode by the first detector and a detection criteria regulator adjusts the detection criteria of the first detector responsive to confirmation results provided by the second detector.

60 Claims, 5 Drawing Sheets

IMPLANTABLE CARDIOVERTER-DEFIBRILLATOR WITH AUTOMATIC ARRHYTHMIA DETECTION CRITERIA ADJUSTMENT

FIELD OF THE INVENTION

The present invention is generally directed to an implantable cardioverter-defibrillator which applies arrhythmia-terminating electrical energy to a heart when an arrhythmic episode is detected. The present invention is more particularly directed to such a device, wherein arrhythmic episode detection criteria are adjusted in response to arrhythmic episode detection confirmation results.

BACKGROUND OF THE INVENTION

Implantable cardioverters-defibrillators, such as implantable ventricular defibrillators, are well known in the art. Such devices include an arrhythmia detector which detects an arrhythmic episode of the heart and an output circuit or generator which applies electrical energy to a heart when an arrhythmic episode is detected to terminate the detected arrhythmia.

The performance of an arrhythmia detector is generally measured by its sensitivity and specificity. Sensitivity is the measure of how well a detector detects all of the arrhythmic episodes. For example, a detector that has a sensitivity of 100% detects all arrhythmic episodes of the type intended to be detected which occur. Specificity, on the other hand, is the measure of how well the detector is able to distinguish or discriminate the arrhythmia intended to be detected from other arrhythmias. For example, an arrhythmia detector which has a specificity of 100% detects only the arrhythmia intended to be detected, and no others.

There are many different types of cardiac arrhythmias. Among these are, for example, ventricular fibrillation, ventricular tachycardia, atrial fibrillation, and atrial tachycardia or flutter. Hence, a ventricular fibrillation detector which is has a sensitivity of 100% and a specificity of 100% is able to detect all ventricular fibrillations episodes that occur (100% sensitive) while at the same time not mistaking any other form of arrhythmic episode for ventricular fibrillation (100% specific).

Although modern implantable cardiovertersdefibrillators employ arrhythmia detectors which have very high sensitivities and specificities, no arrhythmia detector has both a sensitivity and specificity of 100%. Ventricular fibrillation is an immediately life threatening arrhythmia. Hence, all ventricular fibrillation episodes must be detected and, when detected, terminated quickly. As a result, a ventricular fibrillation detector must be very sensitive. In fact, to assure such sensitivity, it is desirable to tolerate some arrhythmic episodes, other than ventricular fibrillation episodes, to be detected as ventricular fibrillation. These are known as false positives.

In order to reduce unneeded, attempted arrhythmic episode terminations, it is well known to provide confirmation of detections. When a ventricular fibrillation episode is initially detected, a storage capacitor which applies the arrhythmia terminating electrical energy to the heart begins charging. Either during or immediately after charging the initial ventricular fibrillation episode detection is confirmed. If confirmation is successful, the arrhythmia terminating electrical energy is immediately applied to the heart. However, if confirmation of the initial ventricular fibrillation episode detection is unsuccessful, the energy delivery is aborted. Such unsuccessful confirmation can, for example, be the result of a false positive in the initial detection or the heart spontaneously returning to a normal rhythm in the short time period between initial detection and unsuccessful confirmation.

The detection parameters or criteria used in the initial detection of ventricular fibrillation episodes represent a difficult tradeoff for the physician. If the number of heartbeats to be analyzed is set too high, there could be a significant delay in the detection of the ventricular fibrillation episodes. If the number of heartbeats to be analyzed is set too low, the confidence that a rhythm detected as ventricular fibrillation truly being ventricular fibrillation is reduced. If the criteria applied to the analyzed beats are set too high, the detection will be overly specific and relatively insensitive resulting in the potential that a ventricular fibrillation episode will go undetected. Lastly, if the criteria applied to the analyzed beats are too low, the opposite problem can occur and the detection will be overly sensitive and relatively unspecific resulting in inappropriate shocks being delivered to the heart.

The present invention addresses these issues. More particularly, as will be seen hereinafter, the confirmation results of the confirmation detection are utilized for the automatic adjustment or regulation of the initial arrhythmia detection criteria to assure maximum sensitivity with appropriate specificity in the initial arrhythmic episode detection parameters or criteria.

SUMMARY OF THE INVENTION

The invention provides an arrhythmia detection system that provides automatic detection criteria adjustment for use in an implantable cardioverter-defibrillator that applies arrhythmia terminating electrical energy to a heart responsive to detection of an arrhythmic episode of the heart. A first detector detects arrhythmic episodes of the heart in accordance with detection criteria. A second detector confirms the detection of each arrhythmic episode by the first detector and a detection criteria regulator adjusts the detection criteria of the first detector responsive to the second detector.

In accordance with one aspect of the present invention, the detection criteria regulator adjusts sensitivity and specificity detection criteria of the first detector. The second, or confirmation detector provides one of successful and unsuccessful confirmation results for each arrhythmic episode detected by the first detector. In accordance with a further aspect of the present invention, the detection system further includes a counter that counts consecutive confirmation results provided by the second detector. The detection criteria regulator adjusts the detection criteria of the first detector in response to the counter counting either at least two consecutive successful confirmation results or two consecutive unsuccessful confirmation results.

In accordance with a further aspect of the present invention the arrhythmia detection system includes a processor, coupled to a ventricular activation detector, that times successive time spans between successive detected ventricular activations and executes an X out of Y routine wherein Y is the total number of successive time spans to be timed for a ventricular arrhythmic episode to be detected and X is the number of time spans shorter than a predetermined time span of the successive number of total time spans required for a ventricular arrhythmic episode to be detected. The detection criteria regulator adjusts the values of X and y.

In accordance with a further aspect of the present invention, the detection system includes a ventricular activation rate variability factor calculator that determines the ventricular activation rate variability. When the ventricular activation rate variability exceeds a given factor, the detection criteria regulator causes the number of heartbeats to be analyzed to be increased or to remain constant.

In accordance with a still further aspect of the present invention, an abort stage causes the application of arrhythmia terminating electrical energy to be inhibited if an arrhythmic episode detection confirmation is unsuccessful. Moreover, the storage capacitor that stores the arrhythmia terminating electrical energy may be reformed when such reforming is required and if a confirmation of an arrhythmic episode detection is unsuccessful.

The invention further provides in an implantable cardioverter-defibrillator that applies arrhythmia detecting electrical energy to a heart responsive to detection of an arrhythmic episode of the heart, an arrhythmia detection system that provides automatic detection criteria adjustment. The system includes first detecting means for detecting arrhythmic episodes of the heart in accordance with detection criteria, second detecting means for confirming the detection of each arrhythmic episode of the first detecting means, and detection criteria regulating means for adjusting the detection criteria of the first detecting means responsive to the second detecting means.

The invention still further provides a method of adjusting arrhythmia episode detection criteria in an implantable cardioverter-defibrillator that applies arrhythmia terminating electrical energy to a heart responsive to detection of an arrhythmia episode of the heart. The method includes the steps of detecting arrhythmia episodes of the heart in accordance with detection criteria, confirming the detection of and providing a confirmation result for each arrhythmia episode detected and adjusting the detection criteria responsive to the confirmation results.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference characters identify identical elements, and wherein:

DETAILED DESCRIPTION OF THE PREFERRED EMBODIMENTS

Figure 1:
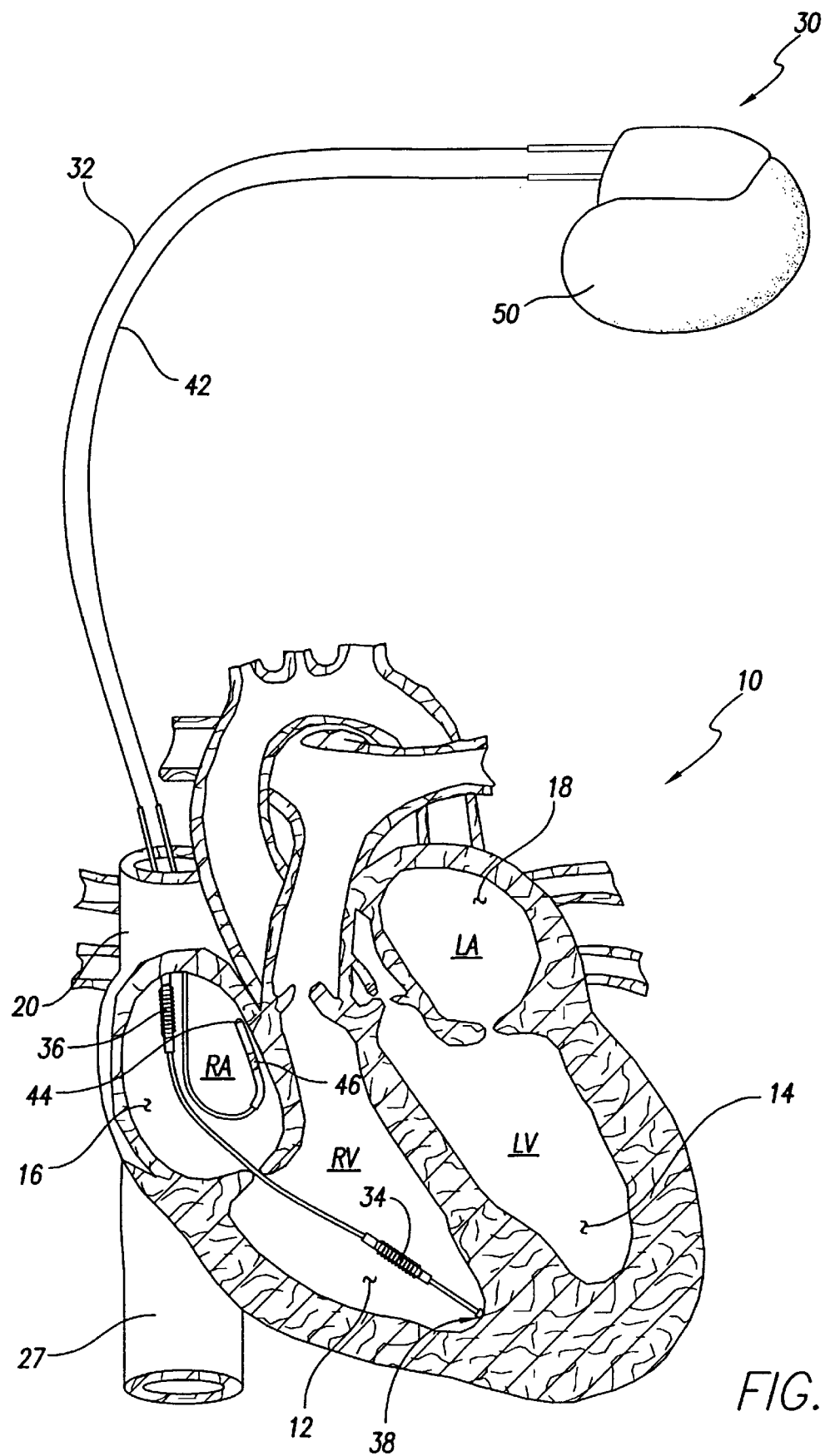
FIG. 1 is a schematic illustration of a human heart in need of ventricular arrhythmia cardioversion-defibrillation shown in association with an implantable ventricular cardioverter-defibrillator embodying the present invention.

Referring now FIG. 1, it illustrates heart 10 in need of ventricular arrhythmia cardioversion-defibrillation and an associated implantable ventricular cardioverter-defibrillator 30 embodying the present invention. The portions of the heart 10 illustrated in FIG. 1 are the right ventricle 12, the left ventricle 14, the right atrium 16, and the left atrium 18. Also illustrated are the superior vena cava 20 and inferior vena cava 27. As is well known in the art, the cardioverter-defibrillator 30 is arranged to be implanted in an upper left chest portion of a patient within a subcutaneous pocket.

The implantable device 30 includes a first endocardial lead 32 which is of the "single-pass" type. To that end, the lead 32 includes a first shock coil 34 arranged to be disposed within the right ventricle 12, a second shock coil 36 proximal to the shock coil electrode 34 and arranged to be disposed within the right atrium 16 or superior vena cava 20, and a distal tip pacing electrode 38. The implantable device 30 further includes a second endocardial lead 42 having an electrode pair including a distal electrode 44 and a proximal electrode 46.

The implantable cardioverter-defibrillator 30 includes a hermetically sealed, electrically conductive enclosure 50. When an quantity of cardioverting or defibrillating electrical energy is applied to the heart 10, in accordance with this preferred embodiment, the electrodes 34 and 36 are connected in parallel and the quantity of arrhythmia terminating electrical energy is applied between the parallel connection of electrode 36 and the electrically conductive enclosure 50 of the implantable device 30 and electrode 34. Alternatively, the cardioverting or defibrillating quantity of electrical energy may be applied between electrode 34 and the electrically conductive enclosure 50 without employing electrode 36. All such cardioverting and defibrillating methodologies apply cardioverting and defibrillating electrical energy to the heart and are thus deemed to be alternative structures and methods in practicing the present invention. Electrodes 44 and 46 of lead 42 support sensing of right atrial electrical activity and delivery of atrial pacing pulses to the right atrium 16.

Figure 2:
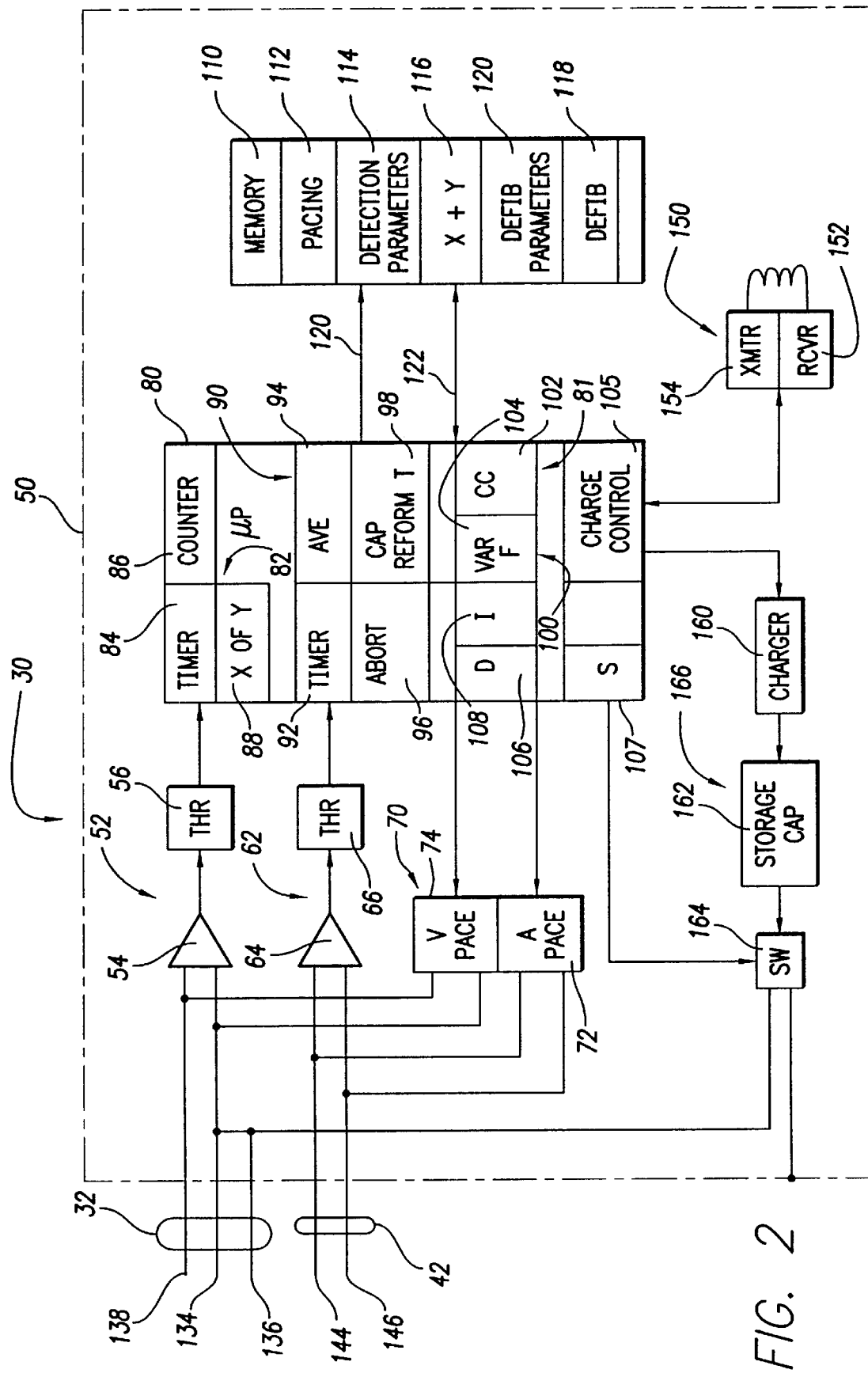
FIG. 2 is a block diagram of the implantable ventricular cardioverter-defibrillator of FIG. 1.

As illustrated in FIG. 2, the implantable cardioverter-defibrillator 30 includes within the enclosure 50 a ventricular sense channel 52, an atrial sense channel 62, and a pacing pulse generator 70 including a first or atrial pacing pulse generator 72 for providing atrial pacing pulses and a second or ventricular pacing pulse generator 74 for providing ventricular pacing pulses. The device 30 further includes a microprocessor 80, a memory 110, and a telemetry stage 150. The device 30 still further includes and cardioversion-defibrillation generator 166 including a charging circuit 160, a storage capacitor 162, and a switch 164.

The ventricular sense channel 52 includes a sense amplifier 54 and a threshold detector 56. The sense amplifier 54 has an input coupled to electrode 38 of lead 32 by a conductor 138 of the lead 32. The sense amplifier 54 has another input which is coupled to electrode 34 of lead 32 by another conductor 134 of the lead 32. The sense amplifier 54 further includes an output which forms an input to the threshold detector 56. As further illustrated, the threshold detector 56 has an output which is coupled to the microprocessor 80.

The sense amplifier 54, together with electrodes 38 and 34 sense electrical activity in the right ventricle 12. When the output from the amplifier 54 transitions through a programmed threshold of the threshold detector 56, the threshold detector 56 provides an input signal to the microprocessor 80 indicating that a ventricular activation or R wave has been detected. Such detection is well known in the art.

Similarly, the atrial sense channel 62 includes a sense amplifier 64 and a threshold detector 66. The sense amplifier 64 has an input which is coupled to electrode 44 of lead 42 by a conductor 144 of lead 42. The sense amplifier 64 has another input which is coupled to the electrode 46 of lead 42 by another conductor 146 of lead 42. As further illustrated, the sense amplifier has an output which forms an input to the threshold detector 66 and the threshold detector 66 has an output which is coupled to the microprocessor 80.

The sense amplifier 64, together with electrodes 44 and 46, sense electrical activity in the right atrium. When the output of the sense amplifier 64 transitions through a programmed threshold of the threshold detector 66, the threshold detector 66 provides an input signal to the microprocessor 80 indicating that an atrial activation or P wave has been detected. Again, such detection is also well known in the art.

The first or atrial pulse generator 72 has outputs coupled to electrodes 44 and 46 of lead 42 by conductors 144 and 146 respectively of lead 42. This permits atrial pacing pulses produced by the atrial pacer 72 to be applied to the right atrium 16. The second or ventricular pulse generator 74 has outputs coupled to electrodes 34 and 38 of lead 32 by conductors 134 and 138 respectively of lead 32. This permits ventricular pacing pulses produced by the ventricular pacer 74 to be applied to the right ventricle 12.

The cardioversion-defibrillation generator 166 applies a quantity of arrhythmia terminating electrical energy to the heart 10. To that end, the charging circuit 160 charges the storage capacitor 162 with the quantity of electrical energy to be applied to the heart upon the detection of a ventricular arrhythmia, such as ventricular fibrillation, as will be described subsequently. The switch 164 applies the quantity of electrical energy from the storage capacitor 162 to the heart. As can be seen in FIG. 2, the switch has an output coupled to electrode 34 of lead 32 by the conductor 134 of lead 32 and another output which is coupled to electrode 36 by a conductor 136 of lead 32. Also, another output of the switch 164 is coupled to the electrically conductive enclosure 50. As a result, when the arrhythmia terminating electrical energy is applied to the heart 10, the electrode 36 is coupled in parallel with the electrical conductive enclosure 50 to provide a return path for current from electrode 34.

The microprocessor 80 controls the overall functioning of the implantable cardioverter-defibrillator 30. To implement such control, the microprocessor executes operating instructions stored in the memory 110 and utilizes various parameters also stored in memory 110. For example, the memory 110 stores the operating instructions defining various pacing modalities which may be provided by the device 30 in a storage location 112. Detection parameters such as the programmable thresholds of threshold detectors 56 and 66 may be stored in storage location 114. As will be seen hereinafter, a ventricular fibrillation detector executes an X out of Y algorithm, and the values of X and Y may be stored in a storage location 116. The operating instructions defining ventricular defibrillation therapy may be stored in a storage location 118. Lastly, defibrillation parameters such as defibrillating energies may be stored in a storage location 120.

The telemetry stage 150 permits modality selections and storage of detection parameters, X and Y values, and defibrillation parameters in the memory 110 to be made through the use of an external programmer (not shown) of the type well known in the art. The telemetry stage includes a receiver 152 which receives telemetry commands including mode selection and parameter commands from the programmer. The receiver 152 conveys the commands to the microprocessor 80 which then stores them in the memory 110. The telemetry stage 150 also includes a transmitter 154. The transmitter may be used for transmitting data to the programmer. The transmitted data may include sensed electograms or status information, for example, as is well known in the art.

The microprocessor 80 is coupled to the memory 110 by a multiple-bit address bus 120 and a bi-directional, multiple-bit data bus 122. The microprocessor 80 uses the address bus 120 to fetch operating instructions or programmable parameters from the memory at address locations defined on the address bus 120. The fetched instructions and parameters are conveyed to the microprocessor 80 over the data bus 122. Similarly, the microprocessor 80 may store data in the memory 110 at memory locations defined on the address bus 120. The microprocessor 80 conveys the data to the memory over the data bus 122. Such microprocessor and memory operation are conventional in the art.

When executing the operating instructions stored in memory 110, the microprocessor implements a number of functional stages in accordance with the present invention. These stages include a first detector 82 including a timer 84, a counter 86, and an X of Y stage 88. The functional stages of microprocessor 80 further include a second detector 90 including a timer 92, an averaging stage 94, an abort stage 96, and a capacitor reform timing stage 98. In addition to the first detector 82 and the second detector 90, the functional stages further include a detection criteria regulator 100 including a confirmation counter 102, a variability factor determining stage 104, a decrementer 106, and incrementer 108. Lastly, the functional stages include a charge control 105 and a synchronizing stage 107. The first detector 82, second detector 90 and detection criteria regulator 100 form an arrhythmia detection system 81 embodying the present invention.

In accordance with a primary aspect of the present invention, when the first detector 82 detects a ventricular fibrillation episode, the charge control 105 causes the charger 160 to begin charging the storage capacitor 162 with the arrhythmia terminating electrical energy. Also, as the storage capacitor 162 is being charged, the second detector 90 executes a ventricular fibrillation confirmation detection. The successful confirmation or unsuccessful confirmation results of the second detector 94 are counted by the confirmation counter 102 of the detection criteria regulator 100. When a predetermined number of consecutive successful or unsuccessful confirmations have occurred, the detection criteria regulator 100 adjusts the sensitivity and specificity of the detection criteria of the first detector 82. If the confirmation is successful, after the storage capacitor 162 is charged to a desired level under control of the charge control 105, the synchronizing stage 107 causes the switch 164 to operate in synchronization with a detected R wave for applying the arrhythmia terminating electrical energy to the heart 10. If the confirmation of the ventricular fibrillation detection is unsuccessful, the abort stage 96 of the second detector will cause the application of the arrhythmia terminating electrical energy to be aborted and hence not applied to the heart 10.

In accordance with this preferred embodiment, the first detector 82 executes an X out of Y algorithm of the type well known in the art. As will be appreciated by those skilled in the art, other methodologies of initial ventricular fibrillation detection may be employed without departing from the present invention. In executing the X out of Y algorithm, the first detector 82 determines if X beats out of the last Y beats were fast. To that end, the timer 84 times time spans between ventricular activations detected by ventricular sense channel 52. The counter 86 counts the time spans that are shorter than a predetermined time span. If X or more of the last Y beats are shorter than the predetermined time span, the first detector 82 will have detected a ventricular fibrillation. The short time spans may be on the order of 200–350 milliseconds. As an example of the above, if X is equal to 12 and Y is equal to 16, the detector 82 will determine if 12 out of the last 16 beats were shorter than the predetermined span time. If 12 or more of the beats of the last 16 beats were shorter than the predetermined time span, the detector 82 will consider ventricular fibrillation to have been detected.

Upon the initial detection of ventricular fibrillation, the charger 160 as previously described begins to charge storage capacitor 162. Also during the charging time, the second or confirmation detector 90 performs another detection to confirm the initial ventricular fibrillation detection. To confirm the original detection, the second detector 94 may, for example, monitor 4 more beats. If the average of these 4 beats is still considered fast, then the original ventricular fibrillation detection will be successfully confirmed and the arrhythmia terminating electrical energy will be applied as previously described. If the average of those 4 beats is considered not to be fast, then the confirmation is unsuccessful and the abort stage 96 will abort the application of the arrhythmia terminating electrical energy. For timing the time spans between the ventricular activations of the 4 beats, the detector 90 includes a timer 92. The averaging stage 94 averages the time spans between the ventricular activations comprising the last 4 beats to provide the average.

Figure 3:
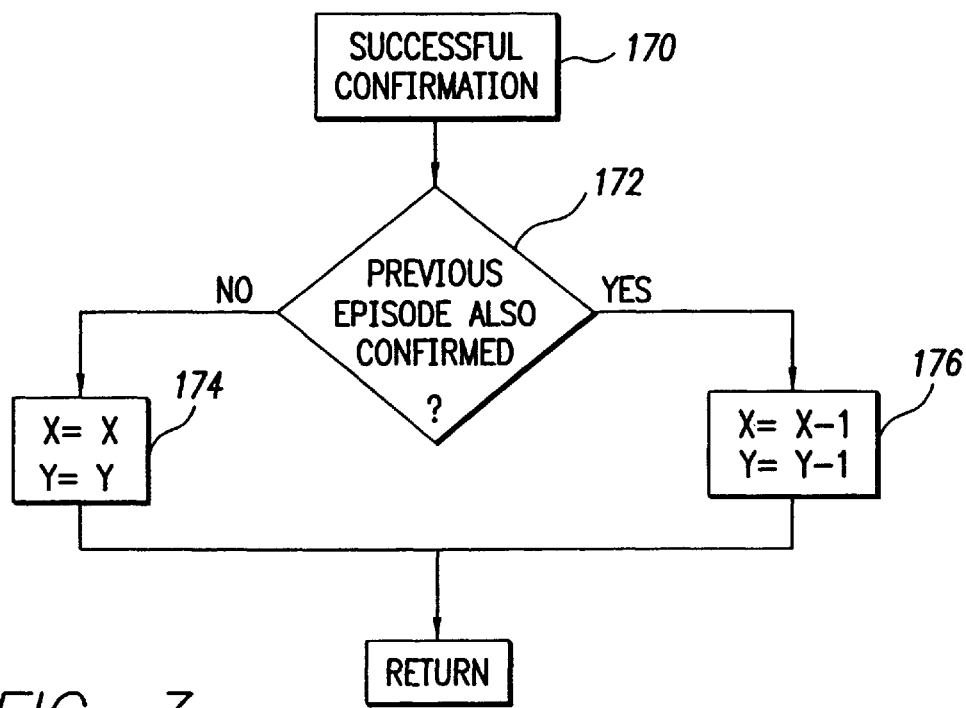
FIG. 3 is a flow diagram illustrating operative steps that the ventricular fibrillation detection system embodying the present invention of the device of FIGS. 1 and 2 may implement in accordance with a preferred embodiment of the present invention for adjusting ventricular fibrillation detection criteria.

Referring now to FIG. 3, it illustrates a flow diagram of the operative steps which may be taken by the detection criteria regulator 100 if there is a successful confirmation of the original ventricular fibrillation episode detection. The first step in the process is step 170 wherein the original detection is confirmed. Next, in step 172, the confirmation counter 102 is addressed to determine if the previous episode was also confirmed. If the previous episode detection was not confirmed, the current values of X and Y in storage location 116 will remain unchanged in accordance with step 174 and the process returns.

If in step 172 it is determined that the previous episode detection was confirmed, in addition to the delivery of the arrhythmia terminating electrical energy, the decrementing stage 106 in step 176 decrements both X and Y in storage location 116 by one.

Following step 176, the process will return.

By decrementing X and Y by one, the detection criteria of detector 82 is adjusted such that the next time it detects an episode, one less heartbeat will be analyzed and one less heartbeat need be fast to satisfy the adjusted ventricular fibrillation detection criteria. This renders the new criteria more sensitive and less specific.

Figure 4:
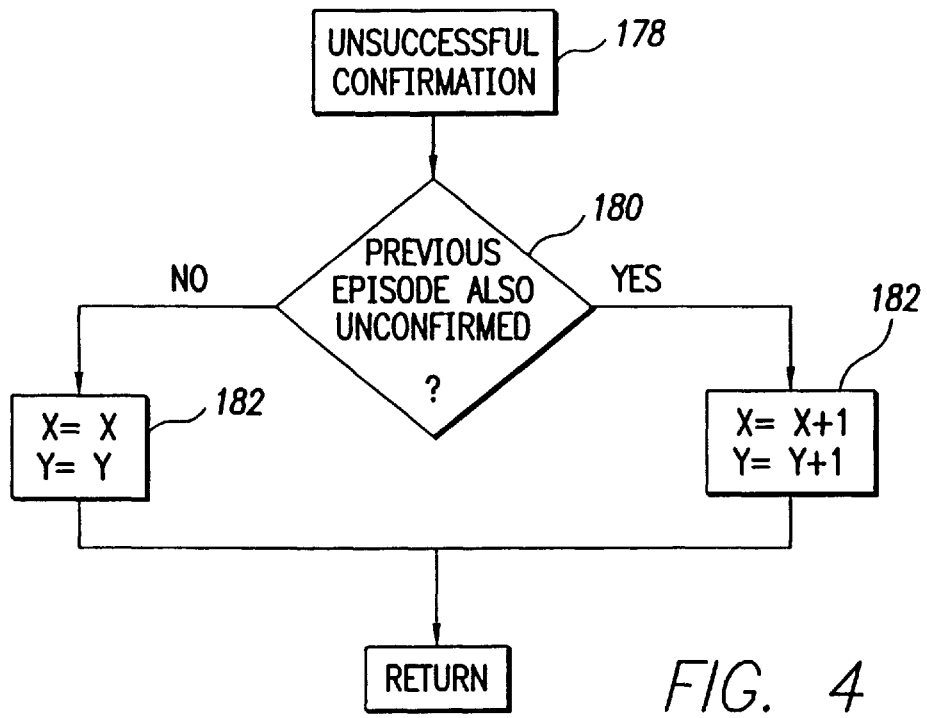
FIG. 4 is another flow diagram illustrating operative steps that the ventricular fibrillation detection system may implement in accordance with the preferred embodiment of the present invention.

Referring now to FIG. 4, it illustrates the operative steps that the detection system may take upon an unsuccessful confirmation. In step 178 it is determined that there has been an unsuccessful confirmation. Next, in step 180 it is determined if the previous episode detection was also unconfirmed. If the previous episode detection was not confirmed, in step 182 the current values of X and Y in storage location 116 are left unchanged and the process returns. However, if in step 180 it is determined that the previous episode detection was also unconfirmed, the values of X and Y in storage location 116 are incremented by one by the incrementing stage 108 in step 182. This causes the adjusted detection criteria of the first detector 82 to be less sensitive and more specific.

Figure 5:
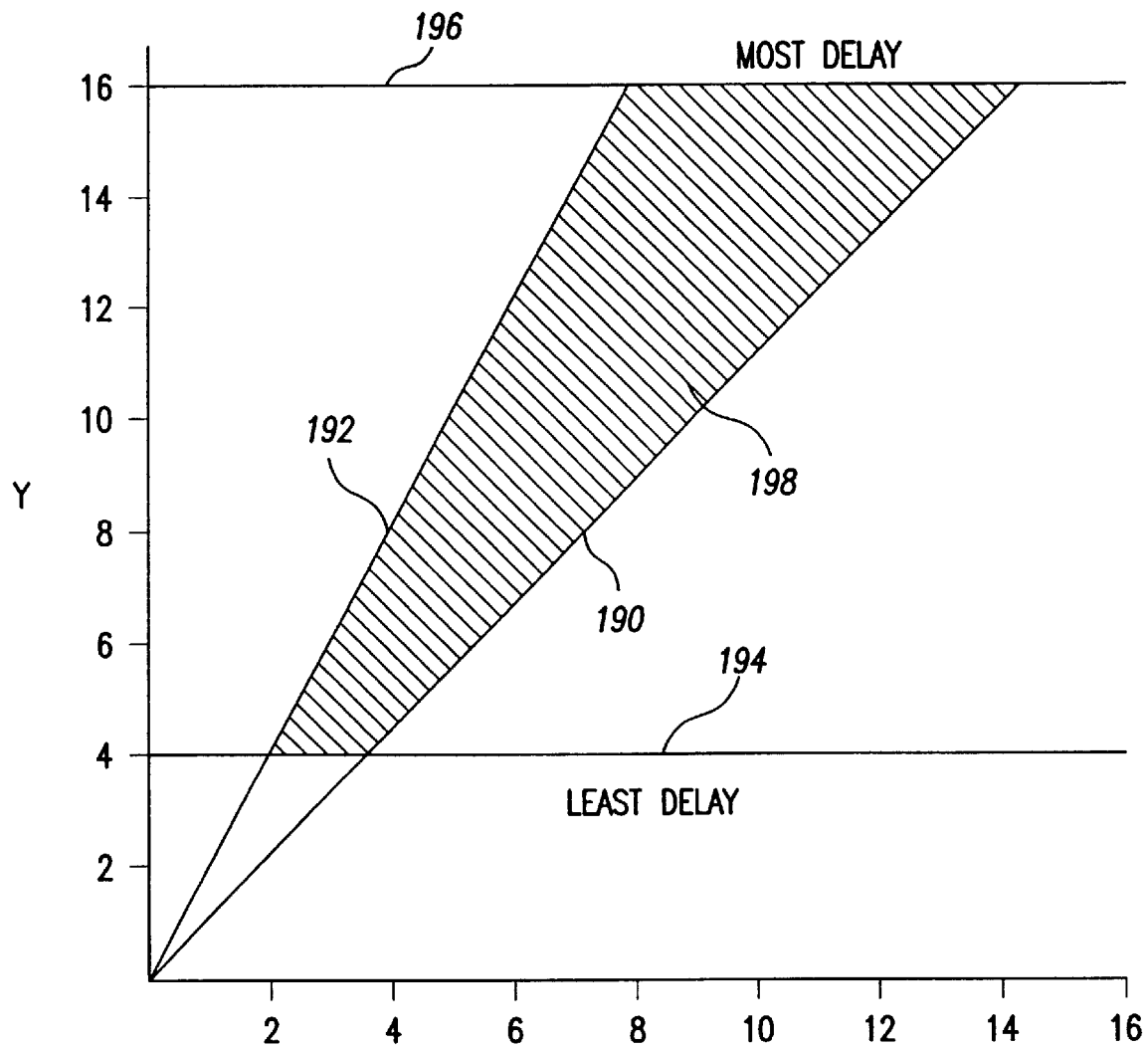
FIG. 5 is a graph illustrating operative ventricular fibrillation detection criteria ranges in accordance with a further aspect of the present invention.

Referring now FIG. 5, it illustrates the present invention in a broader context. It will be noted that the embodiment of the invention described above has the X and Y values being adjusted in lock step. In FIG. 5 an irregular quadrilateral describes an acceptable region for the X and Y values. The X value must be less than a certain extreme to limit the overall delay for detection. In this case, it is shown as a relatively conservative number of 16. The Y value must also be greater than a minimum level to ensure that a certain robust detection takes place. Experience has shown that a value of 4 is probably a minimum. Since X will not be greater than Y, the Y equals X line 190 obtains which is the highest specificity. If one were to assume that at least 50% of the beats should be required to be fast, this results in a high sensitivity line 192 where X is equal to one-half Y. Line 194 is the line of the least detection delay requiring only four beats to be analyzed while line 196 is the line which obtains for the most delay when 16 beats are analyzed for detection. By placing limits on Y and the relationship between X and Y, an acceptable region 198 results for the operation of the first detector as determined by its detection criteria.

Figure 6:
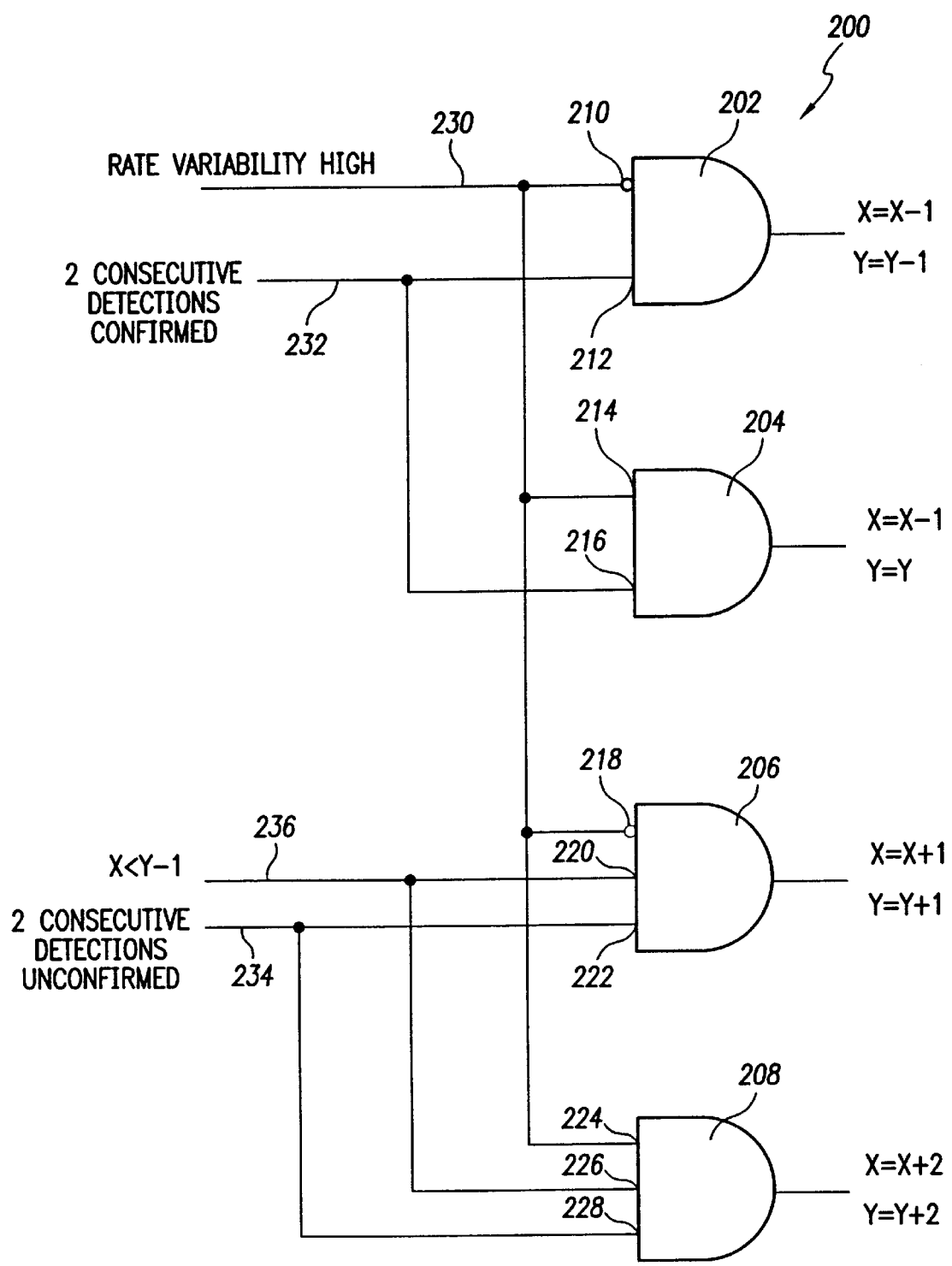
FIG. 6 is a logic diagram illustrating the ventricular fibrillation detection criteria adjustments which may be made in accordance with the present invention in the presence of high and low ventricular rate variabilities.

Referring now to FIG. 6, it illustrates in a logic diagram form the manner in which a detection criteria may be adjusted automatically using a "fuzzy" subset approach. Here it will be noted that a rate variability has been added. The rate variability may be, for example, a coefficient of a variability of the ventricular rate or a standard deviation. The rate variability may be determined by the variability factor determining stage 104 of the detection criteria regulator 100 of FIG. 2.

The logic circuit 200 includes AND gates 202, 204, 206, and 208. AND gate 202 includes an inverting input 210 and an input 212. AND gate 204 includes inputs 214 and 216. AND gate 206 includes an inverting input 218 and inputs 220 and 222. Lastly AND gate 208 includes inputs 224, 226, and 228. Inputs 210, 214, 218, and 224 are coupled together and to a line 230 which is a logical high when the ventricular rate variability factor is high. For example, if the ventricular rate variability factor is a coefficient of a variability greater than, for example, 10%–20%, then the line 230 will be a logical high. Inputs 212 and 216 are coupled to another line 232 which is high when there have been two consecutive successful detection confirmations. Inputs 222 and 228 are coupled to a line 234 which is high when there are two consecutive unsuccessful detection confirmation. Lastly, inputs 220 and 226 are coupled to a line 236 which is high when X is less than Y−1.

As will be noted from FIG. 6, if the coefficient of variability of the rate is low and two detections have been successfully confirmed in a row, then the X and Y values are decremented by one. However, if the coefficient of variability of the rate is high, and two detections have been successfully confirmed, then only the X value is decremented while the Y value is not. In this case, Y is not decremented because the greater variability in the rate requires a larger statistical base to ensure that a representative average is calculated for the rate.

If the coefficient of variability of the rate is low and X is at least one less than Y, and two consecutive unsuccessful confirmations have occurred, than both the X and Y values are incremented. However, if the coefficient of variability of the rate is high, than the X and Y values are both incremented by two. This is to increase the statistical base of the rate to reduce the risk of the detections being aborted merely because of statistical while not raising the percentage of the beats that must be fast.

In accordance with a further aspect of the present invention, the second detector 90 includes a capacitor reform timer 98. In accordance with this aspect of the present invention, if a confirmation is unsuccessful and the capacitor reform is due or almost due as evidenced by the condition of the timer 98, the capacitor 162 would finish charging without being discharged into the heart to allow for the capacitor 162 to be reformed.

While particular embodiments of the present invention have been shown and described, modifications may be made. It is therefore intended in the appended claims to cover all such changes and modifications which fall within the true spirit and scope of the invention.

What is claimed is:

1. In an implantable cardioverter-defibrillator that applies arrhythmia terminating electrical energy to a heart responsive to detection of an arrhythmic episode of the heart, an arrhythmia detection system that provides automatic detection criteria adjustment comprising:

a first detector that detects arrhythmic episodes of the heart in accordance with detection criteria;

a second detector that confirms the detection of each arrhythmic episode by the first detector; and a detection criteria regulator that adjusts the detection criteria of the first detector responsive to the second detector.

2. The arrhythmia detection system of claim 1, wherein the detection criteria includes sensitivity and specificity detection criteria and wherein the detection criteria regulator adjusts sensitivity and specificity detection criteria of the first detector.

3. The arrhythmia detection systems of claim 1, wherein the second detector provides one of successful and unsuccessful confirmation results for each arrhythmia episode detected by the first detector, and wherein the system further includes a counter that counts consecutive confirmation results provided by the second detector and wherein the detection criteria regulator adjusts the detection criteria of the first detector in response to the counter counting at least two consecutive successful confirmation results.

4. The arrhythmia detection system of claim 1, wherein the second detector provides one of a successful and unsuccessful confirmation results for each arrhythmic episode detected by the first detector, and wherein the system further includes counter that counts consecutive confirmation results provided by the second detector and wherein the detection criteria regulator adjusts the detection criteria of the first detector in response to the counter counting at least two consecutive unsuccessful confirmation results.

5. The arrhythmia detection system of claim 1, wherein the implantable cardioverter-defibrillator includes a ventricular activation detector and wherein the first detector is a ventricular arrhythmia detector comprising a processor, coupled to the ventricular activation detector, that times successive time spans between successive detected ventricular activations and executes an X out of Y routine wherein Y is the total number of successive time spans to be timed for a ventricular arrhythmic episode to be detected and X is the number of time spans shorter than a predetermined time span out of the successive number of total time spans required for a ventricular arrhythmic episode to be detected.

6. The arrhythmia detection system of claim 5, wherein the second detector provides one of a successful and unsuccessful confirmation results for each arrhythmic episode detected by the first detector, and wherein the system further includes a counter that counts consecutive confirmation results provided by the second detector and wherein the detection criteria regulator adjusts the detection criteria of the first detector in response to the counter counting at least two consecutive successful confirmation results.

7. The arrhythmia detection system of claim 6, wherein the detection criteria regulator includes a decrementer that decrements X and Y when the counter counts the at least two consecutive successful confirmation results.

8. The arrhythmia detection system of claim 7, wherein the decrementer decrements both X and Y by one.

9. The arrhythmia detection system of claim 7, wherein the detection criteria regulator includes a ventricular activation rate variability factor calculator that determines if a ventricular activation rate variability exceeds a given factor and wherein the decrementer decrements only X when the counter counts the at least two consecutive successful confirmation results and if the ventricular activation rate variability is greater than the given factor.

10. The arrhythmia detection system of claim 9, wherein the decrementer decrements only X by one.

11. The arrhythmia detection system of claim 9, wherein the ventricular activation rate variability factor calculator determines the ventricular activation rate variability corresponding to the Y time spans.

12. The arrhythmia detection system of claim 5, wherein the second detector provides one of a successful and unsuccessful confirmation results for each arrhythmic episode detected by the first detector, and wherein the system further includes a counter that counts consecutive confirmation results provided by the second detector and wherein the detection criteria regulator adjusts the detection criteria of the first detector in response to the counter counting at least two consecutive unsuccessful confirmation results.

13. The arrhythmia detection system of claim 12, wherein the detection criteria regulator includes an incrementer that increments X and Y when the counter counts the at least two consecutive unsuccessful confirmation results.

14. The arrhythmia detection system of claim 13, wherein the incrementer increments both X and Y by one.

15. The arrhythmia detection system of claim 13, wherein the detection criteria regulator includes a ventricular activation rate variability factor calculator that determines if a ventricular activation rate variability exceeds a given factor and wherein the incrementer increments both X and Y when the counter counts the at least two consecutive unsuccessful confirmation results and if the ventricular activation rate variability is greater than the given factor.

16. The arrhythmia detection system of claim 15, wherein the incrementer increments both X and Y by two.

17. The arrhythmia detection system of claim 15, wherein the ventricular activation rate variability factor calculator determines the ventricular activation rate variability corresponding to the Y time spans.

18. The arrhythmia detection system of claim 1, wherein the implantable cardioverter-defibrillator includes a ventricular activation detector, wherein the first detector is a ventricular arrhythmia detector, and wherein the second detector includes a timer that times a given number of consecutive time spans between consecutive detected ventricular activations, an averager that averages the given number of time spans, and wherein the second detector confirms the detection of a ventricular arrhythmic episode if the average of the given number of time spans is less than a predetermined time span.

19. The arrhythmia detection system of claim 1, wherein the cardioverter-defibrillator includes a generator that applies the arrhythmia terminating energy to the heart and wherein the second detector includes an abort stage that causes the generator to be inhibited from applying the arrhythmia terminating energy if the second detector fails to confirm the detection of an arrhythmic episode.

20. The arrhythmia detection system of claim 19, wherein the generator includes a storage capacitor that stores the arrhythmia terminating electrical energy and a capacitor reform timer that determines when the capacitor requires reforming, and wherein the second detector includes a capacitor reform stage that causes the capacitor to store the arrhythmia terminating electrical energy and the generator to be inhibited if the second detector fails to confirm the detection of an arrhythmic episode and if the reform timer determines that the capacitor requires reforming.

21. In an implantable cardioverter-defibrillator that applies arrhythmia terminating electrical energy to a heart responsive to detection of an arrhythmic episode of the heart, an arrhythmia detection system that provides automatic detection criteria adjustment comprising:

first detecting means for detecting arrhythmic episodes of the heart in accordance with detection criteria;

second detecting means for confirming the detection of each arrhythmic episode by the first detecting means; and detection criteria regulating means for adjusting the detection criteria of the first detecting means responsive to the second detecting means.

22. The arrhythmia detection system of claim 21, wherein the detection criteria includes sensitivity and specificity detection criteria and wherein the detection criteria regulating means includes means for adjusting sensitivity and specificity detection criteria of the first detecting means.

23. The arrhythmia detection system of claim 21, wherein the second detecting means includes means for providing one of successful and unsuccessful confirmation results for each arrhythmic episode detected by the first detecting means, and wherein the system further includes counting means for counting consecutive confirmation results provided by the second detecting means and wherein the adjusting means of the detection criteria regulating means adjusts the detection criteria of the first detecting means in response to the counting means counting at least two consecutive successful confirmation results.

24. The arrhythmia detection system of claim 21, wherein the second detecting means includes means for providing one of a successful and unsuccessful confirmation results for each arrhythmic episode detected by the first detecting means, and wherein the system further includes counting means for counting consecutive confirmation results provided by the second detecting means and wherein the adjusting means of the detection criteria regulating means adjusts the detection criteria of the first detecting means in response to the counting means counting at least two consecutive unsuccessful confirmation results.

25. The arrhythmia detection system of claim 21, wherein the implantable cardioverter-defibrillator includes a ventricular activation detecting means for detecting ventricular activations of the heart and wherein the first detecting means is a ventricular arrhythmia detecting means comprising processing means for timing successive time spans between successive detected ventricular activations and for executing an X out of Y routine, wherein Y is the total number of successive time spans to be timed for a ventricular arrhythmic episode to be detected, and X is the number of time spans shorter than a predetermined time span out of the successive number of total time spans required for a ventricular arrhythmic episode to be detected.

26. The arrhythmia detection system of claim 25, wherein the second detecting means includes means for providing one of successful and unsuccessful confirmation results for each arrhythmic episode detected by the first detecting means, and wherein the system further includes counting means for counting consecutive confirmation results provided by the second detecting means and wherein adjusting the means of the detection criteria regulating means adjusts the detection criteria of the first detecting means in response to the counting means counting at least two consecutive successful confirmation results.

27. The arrhythmia detection system of claim 26, wherein the detection criteria regulating means includes decrementing means for decrementing X and Y when the counting means counts the at least two consecutive successful confirmation results.

28. The arrhythmia detection system of claim 27, wherein the decrementing means decrements both X and Y one.

29. The arrhythmia detection system of claim 27, wherein the detection criteria regulating means includes ventricular activation rate variability factor calculating means for determining if a ventricular activation rate variability exceeds a given factor and wherein the decrementing means decrements only X when the counting means counts the at least two consecutive successful confirmation results and if the ventricular activation rate variability is greater than the given factor.

30. The arrhythmia detection system of claim 29, wherein the decrementing means decrements only X by one.

31. The arrhythmia detection system of claim 29, wherein the ventricular activation rate variability factor calculating means determines the ventricular activation rate variability corresponding to the Y time spans.

32. The arrhythmia detection system of claim 25, wherein the second detecting means provides one of successful and unsuccessful confirmation results for each arrhythmic episode detected by the first detecting means, and wherein the system further includes counting means for counting consecutive confirmation results provided by the second detecting means and wherein the detection criteria regulating means adjusts the detection criteria of the first detecting means in response to the counting means counting at least two consecutive unsuccessful confirmation results.

33. The arrhythmia detection system of claim 32, wherein the detection criteria regulating means includes incrementing means for incrementing X and Y when the counting means counts the at least two consecutive unsuccessful confirmation results.

34. The arrhythmia detection system of claim 33, wherein the incrementing means increments both X and Y by one.

35. The arrhythmia detection system of claim 33, wherein the detection criteria regulating means includes ventricular activation rate variability factor calculating means for determining if a ventricular activation rate variability exceeds a given factor and wherein the incrementing means increments both X and Y when the counting means counts the at least two consecutive unsuccessful confirmation results and if the ventricular activation rate variability is greater than the given factor.

36. The arrhythmia detection system of claim 35, wherein the incrementing means increments both X and Y by two.

37. The arrhythmia detection system of claim 35, wherein the ventricular activation rate variability factor calculating means determines the ventricular activation rate variability corresponding to the Y time spans.

38. The arrhythmia detection system of claim 21, wherein the implantable cardioverter-defibrillator includes ventricular activation detecting means, wherein the first detecting means is ventricular arrhythmia detecting means, and wherein the second detecting means includes timing means for timing a given number of consecutive time spans between consecutive detected ventricular activations, averaging means for averaging the given number of time spans, and wherein the second detecting means confirms the detection of a ventricular arrhythmic episode if the average of the given number of time spans is less than a predetermined time span.

39. The arrhythmia detection system of claim 21, wherein the cardioverter-defibrillator includes generating means for applying the arrhythmia terminating energy to the heart and wherein the second detecting means includes abort means for causing the generating means to be inhibited from applying the arrhythmia terminating energy responsive to the second detecting means failing to confirm the detection of an arrhythmia episode.

40. The arrhythmia detection system of claim 39, wherein the generating means includes storage capacitor means for storing the arrhythmia terminating electrical energy and a capacitor reform timing means for determining when the capacitor means requires reforming, and wherein the second detecting means includes capacitor means reform control means for causing the capacitor means to store the arrhythmia terminating electrical energy and the generating means to be inhibited responsive to the second detecting means failing to confirm the detection of an arrhythmia episode and the reform timing means determining that the capacitor means requires reforming.

41. In an implantable cardioverter-defibrillator that applies arrhythmia terminating electrical energy to a heart responsive to detection of an arrhythmic episode of the heart, a method of adjusting arrhythmic episode detection criteria including the steps of:

detecting arrhythmic episodes of the heart in accordance with detection criteria;

confirming the detection of and providing a confirmation result for each arrhythmic episode detected; and adjusting the detection criteria responsive to the confirmation results.

42. The method of claim 41, wherein the adjusting step includes adjusting sensitivity and specificity detection criteria.

43. The method of claim 41, wherein the confirming step includes providing one of successful and unsuccessful confirmation results for each arrhythmic episode detected, and wherein the method further includes counting consecutive confirmation results provided by the confirming step and wherein the adjusting step is performed when at least two consecutive successful confirmation results have been counted.

44. The method of claim 41, wherein the confirming step includes providing one of a successful and unsuccessful confirmation results for each arrhythmic episode detected, and wherein the method further includes counting consecutive confirmation results provided by the confirming step and wherein the adjusting step is performed when at least two consecutive unsuccessful confirmation results have been counted.

45. The method of claim 41, wherein the detecting step includes detecting ventricular arrhythmic episodes and wherein the method further includes the steps of detecting ventricular activations of the heart, timing successive time spans between successive detected ventricular activations and executing an X out of Y routine wherein Y is the total number of successive time spans to be timed for ventricular arrhythmia detection and X is the number of time spans shorter than a predetermined time span out of the successive number of total time spans required for a ventricular arrhythmic episode to be detected.

46. The method of claim 45, wherein the confirming step includes providing one of successful and unsuccessful confirmation results for each arrhythmic episode detected, and wherein the method further includes counting consecutive confirmation results provided by the confirming step and wherein the adjusting step is performed when at least two consecutive successful confirmation results have been counted.

47. The method of claim 46, wherein the adjusting step includes decrementing X and Y when the at least two consecutive successful confirmation results have been counted.

48. The method of claim 47 wherein the decrementing step includes decrementing both X and Y by one.

49. The method of claim 47, including the further step of determining if a ventricular activation rate variability exceeds a given factor and wherein the decrementing step is performed when the at least two consecutive successful confirmation results have been counted and if the ventricular activation rate variability is greater than the given factor.

50. The method of claim 49, wherein the decrementing step includes decrementing only X by one.

51. The method of claim 49, wherein the ventricular activation rate variability factor determining step includes determining the ventricular activation rate variability corresponding to the Y time spans.

52. The method of claim 45, wherein the confirming step includes providing one of successful and unsuccessful confirmation results for each arrhythmic episode detected, and wherein the method further includes counting consecutive confirmation results provided by the confirming step and wherein the adjusting step is performed when at least two consecutive unsuccessful confirmation results have been counted.

53. The method of claim 52, wherein the adjusting step includes incrementing X and Y when at least two consecutive unsuccessful confirmation results have been counted.

54. The method of claim 53, wherein the incrementing step includes incrementing both X and Y by one.

55. The method of claim 53, including the further step of determining if a ventricular activation rate variability exceeds a given factor and wherein the incrementing step is performed when the at least two consecutive unsuccessful confirmation results have been counted and if the ventricular activation rate variability factor is greater than the given.

56. The method of claim 55, wherein the incrementing step includes incrementing both X and Y by two.

57. The method of claim 55, wherein the ventricular activation rate variability factor determining step includes determining the ventricular activation rate variability corresponding to the Y time spans.

58. The method of claim 41, wherein the confirming step includes the steps of detecting ventricular activations of the heart, timing a given number of consecutive time spans between consecutive detected ventricular activations, averaging the given number of time spans, and confirming the detection of an arrhythmic episode if the average of the given number of time spans is less than a predetermined time span.

59. The method of claim 41, including the further step of inhibiting application of the arrhythmia terminating energy upon failing to confirm the detection of an arrhythmic episode.

60. The method of claim 59, wherein the cardioverter-defibrillator includes a storage capacitor that stores the arrhythmia terminating electrical energy and wherein the method further includes the steps of determining if the capacitor requires reforming, causing the capacitor to store the arrhythmia terminating electrical energy and inhibiting the application of the arrhythmia terminating electrical energy upon failing to confirm the detection of an arrhythmic episode and if the capacitor requires reforming.

* * * * *